US00PP27948P2

(12) United States Plant Patent
Hartman

(10) Patent No.: US PP27,948 P2
(45) Date of Patent: Apr. 25, 2017

(54) ***CALADIUM* PLANT NAMED 'MONUMENT'**

(50) Latin Name: *Caladium×hortulanum*
Varietal Denomination: Monument

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,544

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Monument', characterized by its compact, short to intermediate, upright and uniformly mounded plant habit; vigorous growth habit and very rapid growth rate; fancy-type leaves with medium green-colored venation, areas surrounding the veins and margins; white and/or white and pink-colored interveinal areas; and green-colored areas marked with white or pink-colored flecks and speckles; and relatively high yield of the largest grade tubers.

4 Drawing Sheets

Botanical designation: *Caladium×hortulanum.*
Cultivar denomination: 'MONUMENT'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Monument'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium×hortulanum* 'White Christmas', not patented, as the female, or seed, parent with *Caladium×hortulanum* 'Cerise' (known as 'Pha Ya Mol' in Thailand), not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Monument'. These characteristics in combination distinguish 'Monument' as a new and distinct *Caladium* plant:

1. Compact, short to intermediate, upright and uniformly mounded plant habit.
2. Vigorous growth habit and very rapid growth rate.
3. Fancy-type leaves with medium green-colored venation, areas surrounding the veins and margins; white and/or white and pink-colored interveinal areas; and green- colored areas marked with white or pink-colored flecks and speckles.
4. Relatively high yield of the largest grade tubers.

Plants of the new *Caladium* differ primarily from plants of the female parent, 'White Christmas', in the following characteristics:

1. Plants of the new *Caladium* are shorter than plants of 'White Christmas'.
2. Plants of the new *Caladium* and 'White Christmas' differ in leaf color as leaves of 'White Christmas' have distinct dark green-colored venation with white-colored interveinal areas that are often tinged with pink and dark green-colored borders.
3. Leaves of plants of the new *Caladium* are more textured than leaves of 'White Christmas'.
4. Plants of the new *Caladium* and 'White Christmas' differ in leaf petiole color as leaf petioles of 'White Christmas' are green in color with black-colored stripes.
5. Plants of the new *Caladium* produce more tubers of the largest grade sizes than plants of 'White Christmas'.

Plants of the new *Caladium* differ primarily from plants of the male parent, 'Cerise', in the following characteristics:

1. Plants of the new *Caladium* grow faster than plants of 'Cerise'.

2. Plants of the new *Caladium* and 'Cerise' differ in leaf color as leaves of 'Cerise' have green-colored leaves that are overall flushed with deep bronze with black-colored venation surrounded with reddish bronze areas and coral pink-colored interveinal markings.
3. Plants of the new *Caladium* and 'Cerise' differ in leaf petiole color as leaf petioles of 'Cerise' are close to black in color.

Plants of the new *Caladium* can be compared to plants of *Caladium×hortulanum* 'Candidum Senior', not patented. In side-by-side comparisons, plants of the new *Caladium* differ primarily from plants of 'Candidum Senior' in the following characteristics:

1. Plants of the new *Caladium* are more mounding than and not as upright as plants of 'Candidum Senior'.
2. Plants of the new *Caladium* and 'Candidum Senior' differ in leaf color as leaves of 'Candidum Senior' are greenish white in color with medium green-colored venation and thin green-colored margins.
3. Plants of the new *Caladium* produce more tubers of the largest grade sizes than plants of 'Candidum Senior'.

Plants of the new *Caladium* can also be compared to plants of *Caladium×hortulanum* 'Candidum', not patented. In side-by-side comparisons, plants of the new *Caladium* differ primarily from plants of 'Candidum' in the following characteristics:

1. Plants of the new *Caladium* are more mounding than and not as upright as plants of 'Candidum'.
2. Plants of the new *Caladium* and 'Candidum' differ in leaf color as leaves of 'Candidum' have distinct green-colored venation with white-colored interveinal areas; developing leaves of 'Candidum' are mostly green in color with white-colored flecks.
3. Plants of the new *Caladium* and 'Candidum' differ in leaf petiole color as leaf petioles of 'Candidum' are close to black in color with green-colored stripes, stippling and streaks.
4. Plants of the new *Caladium* produce more tubers of the largest grade sizes than plants of 'Candidum'.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Monument' in a container and grown in a shadehouse (tuber not de-eyed).

The photograph at the top of the second sheet is a comparison view of typical potted plants of the male parent, 'Cerise' (left), 'Monument' (center) and the female parent, 'White Christmas' (right).

The photograph at the bottom of the second sheet is a comparison view of typical potted plants of 'Candidum Senior' (left), 'Monument' (center) and 'Candidum' (right).

The photograph at the top of the third sheet is a comparison view of typical plants of 'Monument' grown in containers; the plant on the left has not had its tuber de-eyed and the plant on the right has had its tuber de-eyed prior to planting.

The photograph at the bottom of the third sheet is a side perspective view of typical plants of 'Monument' grown in an open field.

The photograph at the top of the fourth sheet is a close-up view of typical freshly-harvested tubers and roots of 'Monument'.

The photograph at the bottom of the fourth sheet is a close-up view of a typical inflorescence of 'Monument'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old (vegetative plant photographs and description) and eleven weeks old (inflorescence photograph and description), and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Monument'.

Parentage:

*Female, or seed, parent.*—*Caladium×hortulanum* 'White Christmas', not patented.

*Male, or pollen, parent.*—*Caladium×hortulanum* 'Cerise' (known as 'Pha Ya Mol' in Thailand), not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments elliptic to round in shape. Height: About 3.5 cm. Diameter: About 4.2 cm to 6.7 cm. Segment height: About 3.2 cm. Segment diameter: About 2.8 cm to 3.5 cm. Axillary buds, height: About 4 mm to 6 mm. Texture: Thick, starchy; somewhat brittle. Color: Epidermis, freshly-harvested: Close to 159A; outer skin, close to 199B. Epidermis, dried: Close to 200A. Cortical tissue: Close to 4D. Axillary buds: Close to 159A and 27D.

*Root description.*—Thick, fleshy contractile roots; color, close to 155C.

*Rooting habit.*—Low branching; dense.

Plant description:

*Plant type*.—Herbaceous perennial; suitable as a potted plant in containers 15-cm to 25-cm and suitable as a landscape plant in shaded areas.

*Plant and growth habit*.—Compact, short to intermediate, upright and uniformly mounded plant habit; vigorous and dense growth habit; very rapid growth rate, potted plants in finished or saleable form in about seven weeks after planting tubers; leaf petioles and leaves arise from one or more growing points on tubers; petioles mostly upright and arching outwardly with development.

*Plant height, from soil level to top of foliar plane, shadehouse-grown potted plants*.—About 23 cm to 32 cm.

*Plant height, from soil level to top of inflorescences, shadehouse-grown potted plants*.—About 40 cm.

*Plant diameter or spread, shadehouse-grown potted plants*.—About 35 cm to 37 cm.

*Number of shoots per plant, shadehouse-grown potted plants, tubers not de-eyed*.—About two to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 5 cm to 12.8 cm. Width: About 1.4 cm to 1.9 cm. Shape: Narrowly elliptic to wedge-shaped. Apex: Acute. Base: Sheathing the stem. Color, inner surface: Close to N155C faintly tinged with close to 186D, colors and patterns on the outer surface are visible on the inner surface. Color, outer surface: Close to N170D faintly tinged with close to 186D, streaked, stippled and striped with close to 200A to 200B faintly tinged with close to 147D; with development, color becoming closer to 200A to 200B tinged with close to 185C.

Leaf description:

*Arrangement and type*.—Alternate; simple; fancy-type.

*Length, shadehouse-grown potted plants*.—About 17 cm to 20 cm.

*Width, shadehouse-grown potted plants, flattened*.—About 11.5 cm to 14 cm.

*Shape*.—Ovate.

*Apex*.—Acute to acuminate.

*Base*.—Sagittate to peltate.

*Margin*.—Entire; wavy with broad undulations.

*Texture, upper and lower surfaces*.—Smooth, glabrous; somewhat rugose.

*Luster, upper surface*.—Dull sheen.

*Luster, lower surface*.—Glaucous, dull sheen.

*Venation pattern*.—Pinnate.

*Color, shadehouse-grown potted plants*.—Developing leaves, upper surface: Midvein and primary venation: Close to 137A. Areas surrounding venation: Close to 137A and close to 137A with variable flecks, close to 155C. Margins: Towards the margins, close to 137A; at the margins, close to 187B. Basal notch: Close to 187C. Point of petiole attachment: Close to N186A. Interveinal areas: Close to 193C and 155C; and close to 155C variably tinged with close to 48D and 49C. Developing leaves, lower surface: Midvein: Close to 148C variably tinged with close to 182B. Primary veins: Close to 148B to 148C. Areas surrounding venation: Close to 191A and 191C. Margins: Towards the margins, close to 191A; at the margins, close to 187B. Basal notch: Close to 187C to 187D. Point of petiole attachment: Close to 187C to 187D. Interveinal areas: Close to 155C and close to 155C variably tinged with close to 54C, 54D and 186D; also areas of 191A, 191C, 191D, 148B, 148C, 194B and 194C. Fully expanded leaves, upper surface: Midvein and primary venation: Close to 137A. Areas surrounding venation: Close to 137A and close to 137A with variable flecks, close to 145D and 155C. Margins: Towards the margins, close to 137A and 137B with variable flecks of close to 155C, 146B, 48D and 49C; thin margin, close to 187B. Basal notch: Close to 187B. Point of petiole attachment: Close to N186A to N186B. Interveinal areas: Close to whiter than 155C; close to 155C variably tinged with close to 48D and 186D; and close to 145D, 146A and 146B. Fully expanded leaves, lower surface: Midvein: Close to 148C to 148D. Primary veins: Close to 148B. Areas surrounding venation: Close to 191A, 191C, 193B, 148B and 148D. Margins: Towards the margins, close to 191A; at the margins, close to 187B. Basal notch: Close to 187C. Point of petiole attachment: Close to 187B to 187C. Interveinal areas: Close to 155C variably tinged with close to 54C and 186D.

*Petioles*.—Aspect: Initially upright and straight; with development, arching outwardly; flexible. Length, shadehouse-grown potted plants: About 16 cm to 27 cm. Diameter, distally, shadehouse-grown potted plants: About 4 mm to 4.5 mm. Diameter, proximally, shadehouse-grown potted plants: About 7 mm to 9 mm. Texture: Smooth, glabrous; glaucous. Color, shadehouse-grown potted plants: Close to 199B and N170D; faintly tinged with close to 186D; stippled, streaked and tessellated with close to 200A to 200B faintly tinged with close to 147D; below the leaf and petiole junction, close to 145A and 194B variably streaked, stippled and tessellated with close to 200D or 147B to 147C. Wing length, shadehouse-grown potted plants: About 4 cm to 7 cm. Wing diameter, shadehouse-grown potted plants: About 4 mm to 9 mm. Texture, inner and outer surfaces: Smooth, glabrous. Luster, inner and outer surfaces: Dull. Wing color, shadehouse-grown potted plants: Inner surface: Close to N155C occasionally tinged with close to 186D; colors and patterns on the outer surface are visible on the inner surface. Outer surface: Close to N170D and 194A tinged with close to 147B; streaked, stippled and tessellated with close to 147A or 200A.

Inflorescence description: Inflorescences observed on eleven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring and summer in central Florida; flowers develop about eleven weeks after growth commences; inflorescences last about three days before fading; inflorescences persistent.

*Spathe*.—Length, overall: About 12.7 cm. Length, distal open portion: About 8.2 cm. Length, proximal closed portion: About 4.5 cm. Width, distal open portion: About 4.7 cm. Depth, distal open portion: About 3 cm. Width, at constriction: About 1.4 cm. Width, proximal closed portion: About 2.5 cm. Shape: Elliptic to slightly obovate. Apex: Acuminate. Base: Obtuse. Margin: Entire; slightly recurved. Texture, front and rear surfaces: Smooth, glabrous. Luster, front surface: Dull sheen. Luster, rear surface: Slightly glaucous, dull sheen. Color, front surface: Distal open portion: Whiter than 155C; margins occasionally faintly tinged with close to 145D; with development, color becoming closer to N199A. Proximal closed portion: Close to 147D tinged with close to 138B; towards the base, streaked and flushed with close to 187A and 187B; color does not change with development. Color, rear surface: Distal open portion: Close to 155C; center, faintly marbled with close to 155D and 150D; color does not change with development. Proximal closed portion: Close to 138B and 147D marbled with close to 138B to 138C; margins, flecked and streaked with close to 155C and 145D; color does not change with development.

*Spadix*.—Length, overall: About 9.7 cm. Length, male flower zone: About 5.8 cm. Length, sterile zone: About 1.9 cm. Length, female flower zone: About 2 cm. Diameter, male flower zone: About 1.1 cm. Diameter, sterile flower zone: About 6 mm. Diameter, female flower zone: About 1 cm. Shape: Columnar, spindle-shaped. Apex: Acute. Base: Obtuse. Aspect: Upright. Color, mature, male zone: Close to 158D. Color, mature, sterile zone: Close to 159D. Color, mature, female zone: Close to 159A. Male flowers: Quantity per spadix: About 185. Shape: Obovate. Height: About 3.2 mm. Diameter: About 3 mm. Pollen amount: Moderate. Pollen color: Close to 10D. Female flowers: Quantity per spadix: About 220. Shape: Ovate. Height: About 2.5 mm. Diameter: About 1.5 mm. Stigma color: Close to 158D. Ovary color: Close to 159A.

*Scape*.—Length: About 27.3 cm. Diameter: About 6 mm. Strength: Sturdy; flexible. Aspect: Mostly erect. Texture: Smooth, glabrous. Luster: Glaucous. Color: Close to 199C to 199D and close to N170D stippled, streaked and tessellated with close to 200A to 200B and faintly tinged with close to 147D; just below spathe, close to 138B and 147C to 147D tinged with close to 146D.

*Seeds and fruits*.—To date, seed and fruit development have not been observed on plants of the new *Caladium*.

Disease & pest tolerance: Plants of the new *Caladium* have been observed to have average tolerance to *Xanthomonas* Leaf Spot and *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Monument' as illustrated and described.

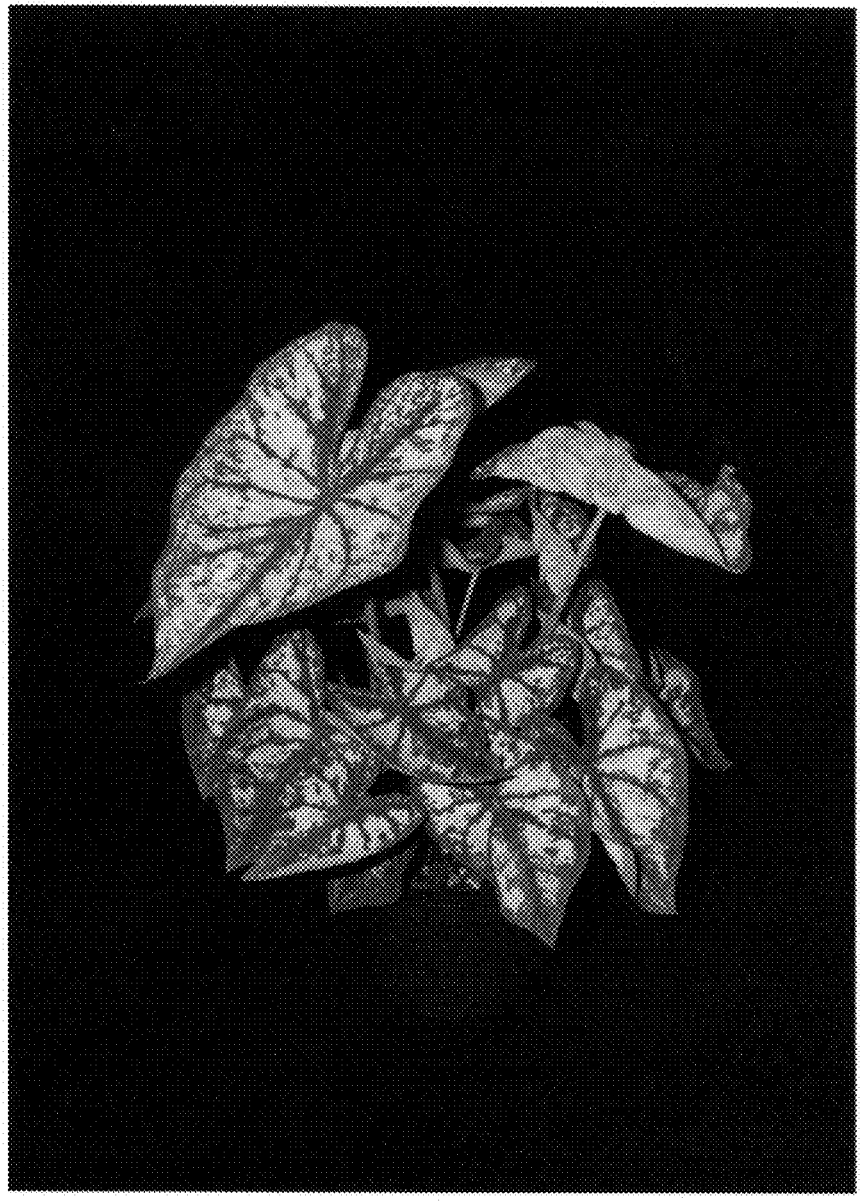

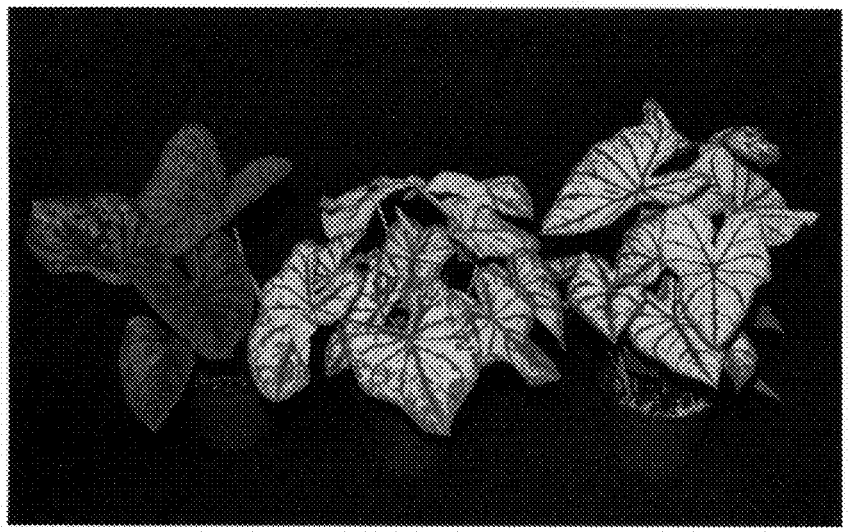
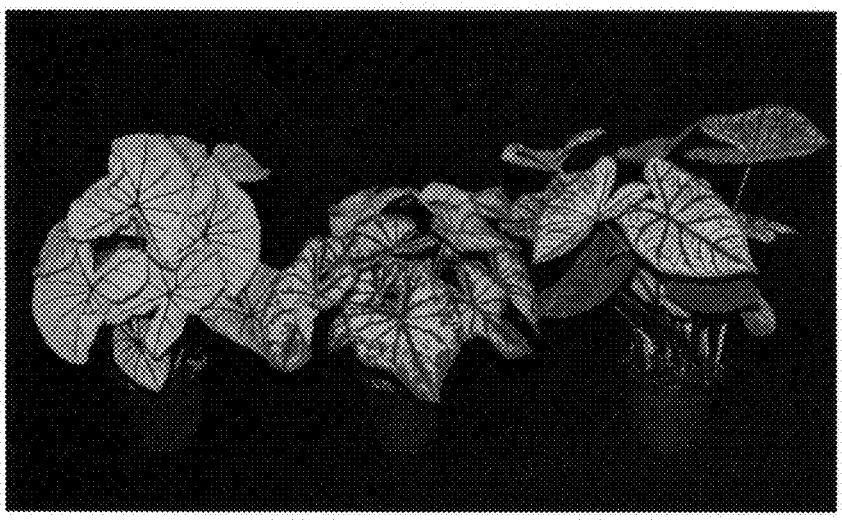

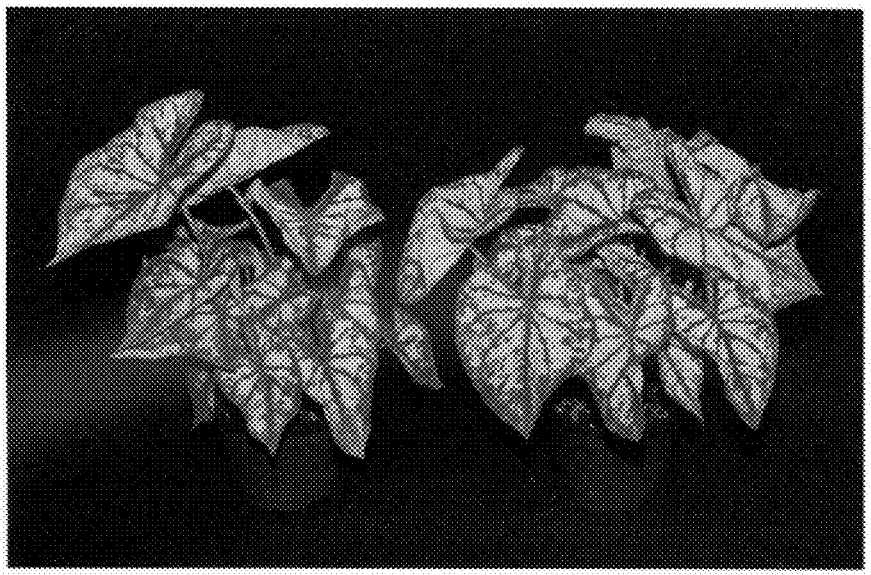
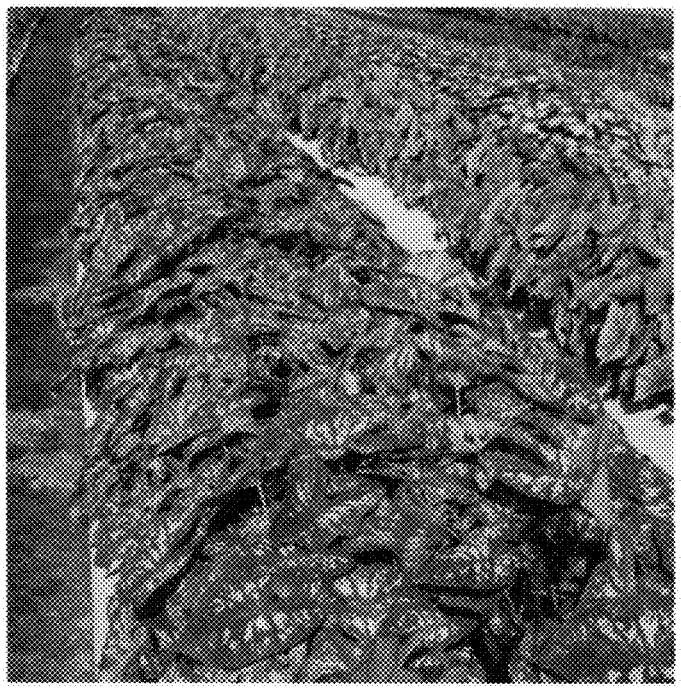

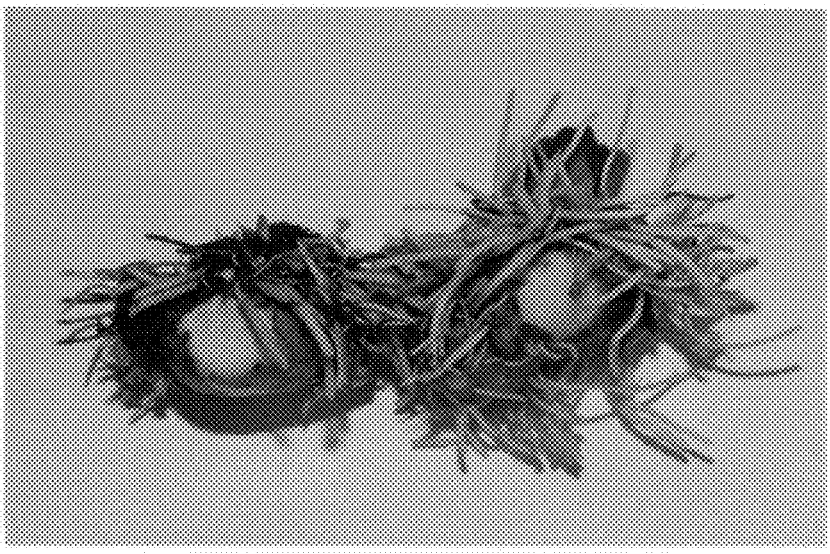
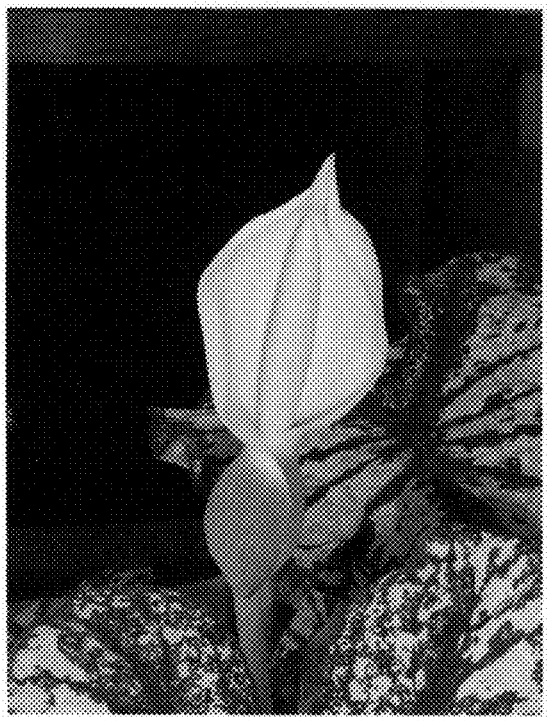

* * * * *